(12) United States Patent
Kucharczyk et al.

(10) Patent No.: US 8,182,607 B2
(45) Date of Patent: May 22, 2012

(54) IN-SITU CRYSTALLINE MATERIAL SCREENING APPARATUS AND METHOD

(75) Inventors: Damian Kucharczyk, Glowna (PL); Richard Cooper, Didcot (GB); Paul William Loeffen, Steventon (GB)

(73) Assignee: Agilent Technologies, Inc., Santa Clara, CA (US)

( * ) Notice: Subject to any disclaimer, the term of this patent is extended or adjusted under 35 U.S.C. 154(b) by 1406 days.

(21) Appl. No.: 11/610,257

(22) Filed: Dec. 13, 2006

(65) Prior Publication Data

US 2007/0140421 A1 Jun. 21, 2007

(51) Int. Cl.
*C30B 35/00* (2006.01)
*G01N 23/207* (2006.01)

(52) U.S. Cl. .......... 117/200; 117/201; 117/203; 117/14; 117/925

(58) Field of Classification Search .................. 117/200, 117/201, 203, 14, 925
See application file for complete search history.

(56) References Cited

U.S. PATENT DOCUMENTS

| | | | |
|---|---|---|---|
| 2002/0067800 A1* | 6/2002 | Newman et al. | 378/73 |
| 2003/0170999 A1* | 9/2003 | Myerson | 438/712 |
| 2004/0062691 A1* | 4/2004 | Haushalter et al. | 422/245.1 |

OTHER PUBLICATIONS

Otwinowski et al. "Processing of X-ray Diffraction Data Collected in Oscillation Mode," Method of Enzymology, vol. 276, 1997, p. 307-326.*

* cited by examiner

*Primary Examiner* — Matthew Song

(57) ABSTRACT

There is provided a method and apparatus for assessing in-situ crystal formation in a test sample. Both optical imaging and X-ray diffraction techniques are utilized, with the results of these processes being combined in such a way as to produce an overall score relating to the aptness of crystalline material for harvesting and subsequent X-ray crystallography.

11 Claims, 9 Drawing Sheets

Fig.5.

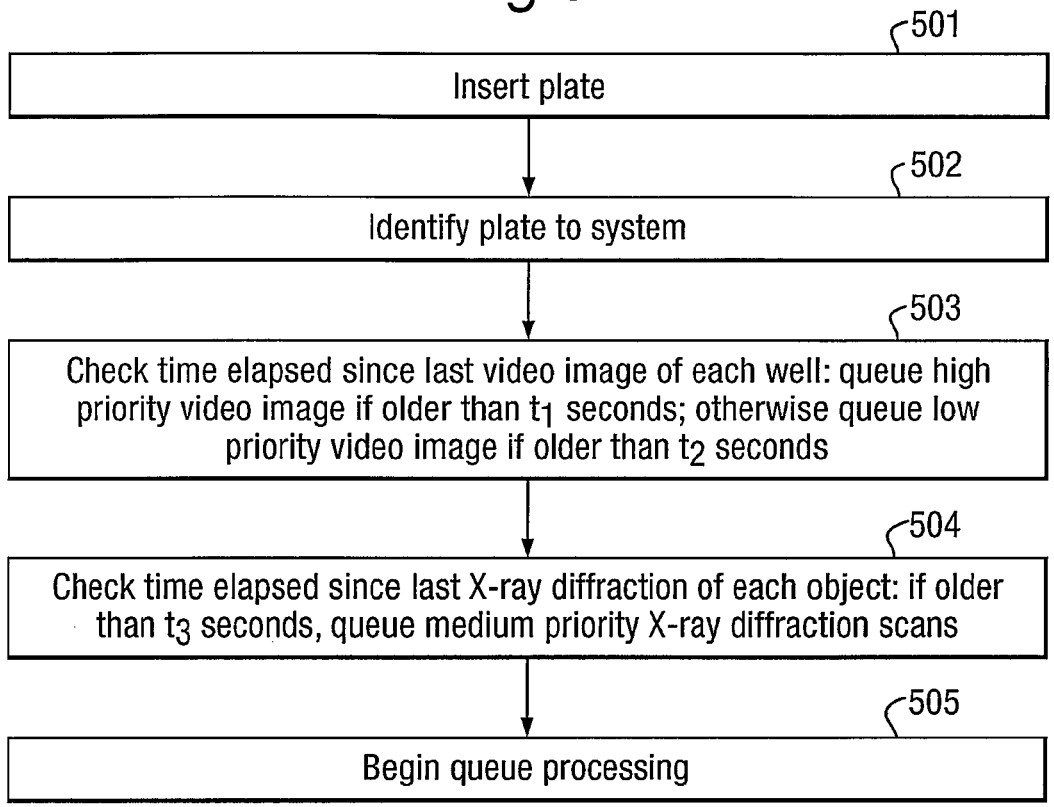

501 — Insert plate

502 — Identify plate to system

503 — Check time elapsed since last video image of each well: queue high priority video image if older than $t_1$ seconds; otherwise queue low priority video image if older than $t_2$ seconds 504 — Check time elapsed since last X-ray diffraction of each object: if older than $t_3$ seconds, queue medium priority X-ray diffraction scans 505 — Begin queue processing

Fig.6.

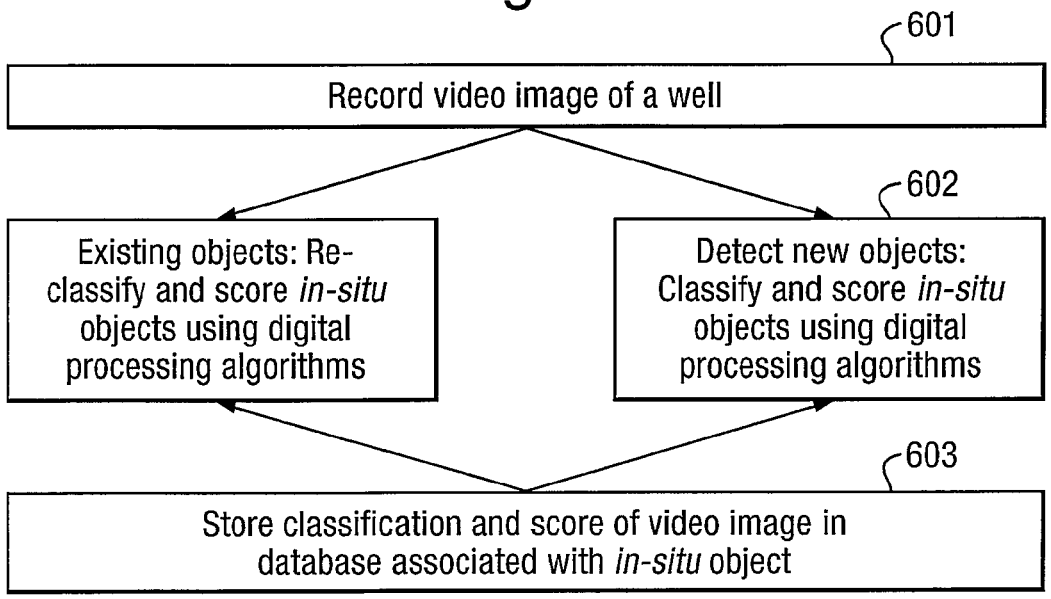

601 — Record video image of a well

Existing objects: Re-classify and score in-situ objects using digital processing algorithms 602 — Detect new objects: Classify and score in-situ objects using digital processing algorithms 603 — Store classification and score of video image in database associated with in-situ object

IN-SITU CRYSTALLINE MATERIAL SCREENING APPARATUS AND METHOD

FIELD OF THE INVENTION

This present invention relates generally to the field of X-ray diffraction, and in particular to the field of X-ray crystallography.

BACKGROUND OF THE INVENTION

X-ray crystallography is a technique that is widely used to obtain information about the structure of molecules. The technique exploits the characteristic diffraction of X-rays from crystals such that three-dimensional models may be generated of the constituent molecules of the crystal, which are consistent with the observed diffraction.

X-ray crystallography is often used in the context of biological research to establish the three dimensional structure of molecules of interest, and, in particular, that of proteins. In this context, X-ray crystallography is often referred to as protein crystallography. Recently there has been a significant international investment in the techniques of protein crystallography including protein production, purification, crystallisation, X-ray diffraction, data reduction and structure solution leading to "high-throughput" approaches. Despite this the technique often remains cumbersome with a high attrition rate in getting from expressed protein to structure.

A particularly laborious bottleneck is the crystallisation process by which the generation of single crystals suitable for X-ray crystallography from sparse quantities of protein in a liquid medium is attempted. A typical method for crystallisation of proteins is vapour diffusion, for example the "hanging drop" or "sitting drop" methods, whereby microliter or nanoliter drops of a protein and crystallisation reagent in solution are introduced to a well containing a reservoir of crystallisation reagent in solution at a higher concentration. There is only a short distance between the drop and the reservoir solution in the same well. The well is then sealed and due to different concentrations of the droplet and reservoir solution, water diffuses out of the droplet and protein crystals may form. Other crystallisation techniques include the microbatch technique, the dialysis technique, and the gel crystal growth method.

Typically single crystals are grown in containers with a plurality of wells, with each well containing droplets of different crystallisation solutions and/or different proteins. Frequently, in instances where the optimal crystallisation conditions are not known, the multi-well containers may be set up to screen a range of crystallisation conditions with, for example, a range of concentrations of crystallisation solutions, or pH, or other parameters. Crystalline material may form in some of the wells over a period of days or weeks. In such cases it is necessary to identify those wells in which crystals have formed such that the crystal growth conditions may be scaled up with larger quantities of the crystal material; e.g. protein. Such identification is difficult since the crystals may be very small (of the order of 1-50 microns in length). Traditionally this identification has been carried out with an optical microscope to visually identify crystalline material but information may also be gained by other techniques such as light scattering. Manual inspection is labour intensive and very slow given the large number of wells to be inspected, and re-inspected, at regular intervals. Recently, the optical identification of crystals in multi-well containers has been automated via image recognition techniques and numerous automatic or semi-automatic optical scanners are now commercially available (for example Rhombix Vision from Thermo Electron Corp., Minstrel from Rigaku Corporation, Crystal Farm from Bruker Biosciences Inc.).

Following the identification of optimal crystallisation conditions via screening, the crystal growing procedure may be scaled up with larger volumes of the material to be crystallised in the same type of multi-well containers, in the hope of growing larger crystals. In the case of proteins this may require milligrams of pure protein per well. It is then necessary to identify the crystals forming in the wells which have the highest diffraction quality. Typically this is also done using optical inspection, either manually or automatically using the same commercial products as for the crystallisation screening described above.

Finally, following the screening of crystallisation conditions, and the scaling up of the crystal growth, the most promising crystals must be harvested. This is usually done by manipulating the crystal into a cryosolution by hand and then into a cryoloop, or a capillary, such that the crystal may be mounted in an X-ray beam for observation of the diffraction quality of the crystal. Harvesting of the crystal is a particularly labour-intensive step and runs the risk that the fragile crystal will be damaged.

It is clearly of vital importance that those crystals growing successfully for the purpose of X-ray crystallography are accurately identified. As mentioned above, conventional techniques rely on optically inspecting the samples, whether manually or using an automated process. However, current optical inspection methods have a number of critical drawbacks:

Optical inspection cannot reliably identify objects growing in a liquid medium if there is little or no optical contrast.

Optical inspection cannot reliably distinguish whether objects growing in a liquid medium are crystals or amorphous material.

Optical inspection cannot reliably distinguish whether crystals growing in a liquid medium are of the material of interest or not; for example in protein crystallography, instead of protein crystals, it is very common that salt crystals may form, or in the case of protein-ligand complexes it is very common that the small molecules of the ligand may crystallise rather than the complex.

Optical inspection cannot assess the diffraction quality of a single crystal growing in a liquid medium; optical inspection can only infer the diffraction quality from the physical shape and size of the crystal, which often gives false positives, whereas the true diffraction quality can only reliably be ascertained using an X-ray beam.

X-ray screening techniques have been suggested to overcome a number of the flaws inherent in optical screening. Preferably, these techniques will screen individual crystals in their growth environment (i.e. in situ). For example, U.S. patent application Ser. No. 10/042,929 describes an apparatus consisting of an X-ray source and an X-ray detector disposed on opposite sides of a crystal growing incubator. However, this technique is limited to ascertaining the presence or absence of diffracting material, and cannot reliably judge the diffraction quality. Furthermore, the nature of the diffraction material cannot be reliably identified using this technique. For example, the presence of salt crystals (in place of the desired protein crystals) will only be detected if the crystal is fortuitously aligned such that a Bragg condition is satisfied for one of its planes. Similar techniques are disclosed in U.S. Pat. Nos. 6,836,532 and 6,859,520 and are subject to equivalent limitations.

Moreover, X-ray screening techniques are constrained by their very nature. Inherent in any X-ray technique relying on the principles of diffraction is an inability to establish vital practical details such as the morphology of the crystal, the crystal size, and the proximity of the crystal to other objects in the droplet cannot easily be established by X-ray diffraction. Such factors are clearly essential when considering practical matters such as the ability to harvest and mount the crystal for X-ray crystallography.

The drawbacks in both optical and X-ray inspection techniques mean that very frequently the screening of crystallisation conditions can lead to false-positives, which itself leads to a costly waste of time and material attempting to scale up the growing conditions, only to find out after the object is harvested that it is not a crystal of the material of interest, or that the diffraction quality is poor. Furthermore, if the diffraction quality is shown to be poor after harvesting, it is currently not possible to know whether the harvesting process itself damaged the fragile crystal and reduced the diffraction quality.

There is consequently a need in the field to reliably identify crystals of the material of interest both in the early screening of crystallisation conditions, as well as after the growing conditions have been scaled up. There is also a need in the field to reliably assess the suitability of putative crystals for X-ray crystallography in the wider sense before they are harvested from the liquid medium in which they are grown.

SUMMARY OF THE INVENTION

According to the first aspect of the present invention, there is provided a screening apparatus for assessing in-situ crystal formation in a test sample, the apparatus comprising: optical imaging means for obtaining optical image data from the test sample; X-ray diffraction apparatus for obtaining X-ray diffraction data from the test sample, the X-ray diffraction apparatus and the optical imaging means mounted within a common housing; processing means coupled to the optical imaging means and the X-ray diffraction apparatus, the processing means adapted to compute an optical image quality parameter from the optical image data and an X-ray diffraction quality parameter from the X-ray diffraction data, the processing means further adapted to compute a crystallographic aptness parameter from the optical image quality parameter and the X-ray diffraction quality parameter, the crystallographic aptness parameter being a measure of the suitability of crystalline material in the test sample for subsequent harvesting and X-ray crystallography; and support means for mounting the test sample within the apparatus, the support means comprising integral translation means for moving the test sample between the optical imaging means and the X-ray diffraction apparatus.

The present invention provides an automated system for screening growing crystals in situ. The use of both optical and X-ray screening techniques avoids the risk of false positives inherent in the use of either one of these techniques alone. The crystallographic aptness score generated by the present invention thus genuinely reflects the usefulness of the crystal for its intended purpose, indicating the precision with which the three dimensional molecular structure may be determined by X-ray crystallography.

The present invention employs both the optical images and the X-ray diffraction images to generate a combined quantitative scoring of the Crystallographic Aptness of putative crystals. Thus the information from the X-ray diffraction analysis augments the information from the optical image alone. Conversely, the optical image provides additional information about the Crystallographic Aptness of a crystal that cannot be easily derived from the X-ray diffraction image alone, including the morphology of the crystal, the crystal size, the proximity of the crystal to other objects in the droplet etc. Combining the analysis of both optical and X-ray images therefore allows an enhanced quantitative assessment that neither method can provide in isolation. For example, a crystal which scores highly for size and morphology may yield a low score from the X-ray diffraction images—giving a low overall score for the Crystallographic Aptness. Conversely, a crystal which scores highly for in situ X-ray diffraction may be bound in a cluster of crystals visible by optical inspection thereby making it impractical to harvest—consequently this would give a lower overall score for Crystallographic Aptness than for a well separated crystal.

The use of X-ray screening allows the present invention to positively confirm whether objects identified by optical methods are crystalline or not; for example amorphous material can easily be distinguished in a way that is not possible using only optical methods.

The optical image quality parameter is affected by, for example, the physical size and morphology of crystals and, in the case of crystals in their growth medium, the separation from other crystals since this determines the practical ability to harvest and mount the crystal for X-ray crystallography. Such properties are best probed optically and may lead to a measure of optical image quality.

The X-ray diffraction quality parameter is affected by, for example, the mosaicity which describes the integrity of packing of crystalline domains, and furthermore can be characterised by, for example, the resolution limit of the X-ray diffraction and the ability to index the diffraction. Such properties can only be probed using X-rays and may lead to a measure of X-ray diffraction quality.

A preferred embodiment of the present invention comprises a rotational axis defined by the intersection of the support means and the X-ray diffraction apparatus, wherein the translation means is adapted to move the support means parallel and perpendicular to the rotational axis. Preferably, the X-ray diffraction apparatus comprises an X-ray source, and the rotational axis is perpendicular to a beam path between the X-ray source and the support means. In this preferred embodiment, it is this movement that allows the test sample to be aligned accurately with the optical imaging means and the X-ray diffraction apparatus.

Preferably, the X-ray diffraction apparatus is adapted to obtain an oscillation image from the test sample. An oscillation image is obtained by scanning the sample through an angle and leads to peaks in the intensity of the detected X-rays as the sample passes through the angle at which the Bragg criteria is satisfied for one of the crystal planes. The nature of the crystalline structure can then be deduced from the number and location of the intense peaks. In addition to giving more information with which to judge the suitability of a crystal for X-ray diffraction, a consequence of oscillation imaging is that false positives caused by salt crystals can be identified and discarded. Indeed, through the use of oscillation imaging, the system of the present invention is able not only to distinguish between salt crystals and crystals of the material of interest (particularly proteins), but also, in the case of protein-ligand complexes, the system can positively discriminate between crystals of the ligand and crystals of the protein.

In a preferred embodiment of the present invention, the translation means is adapted to rotate the support means around the rotational axis. This facilitates the creation of an oscillation image and, furthermore, may be used to focus the sample within the optical imaging means.

Often, more than one crystal will grow in a given test sample. Since it is necessary to test each crystal individually both the optical imaging means and the X-ray diffraction apparatus are preferably able to assess the crystal formation of only a small part of the test sample.

A preferred embodiment of the present invention is capable of calculating the crystallographic aptness parameter of a plurality of samples within an array. Preferably, the present invention is able to optimise the order in which samples in the array are examined. For example, optical image data may be obtained and stored for each test sample and the objects found in test samples then preferably queued for X-ray diffraction in an order that depends on the computed optical image quality parameter for each test sample. The container may be a multiwell container or any other container in which crystals are grown.

The present invention may comprise means to store the time and result of previous tests on a given sample. This data may be used to automate the performance of the next test. For example, a sample may be queued for further testing when it has not been tested for a predetermined period of time. Moreover, the results of previous tests may be used to give the most promising samples a higher priority for further testing than other samples.

The present invention is also preferably capable of tracking the progress of crystal samples as they are grown. This can be done by observing the crystal on a plurality of occasions during its growth. The ability to track crystal growth from its early stages through to the point of harvesting helps to optimise the crystal growth conditions. It finds particular utility in, for example, determining the optimum amount of time to soak a protein crystal with a small molecule in order to produce a co-crystal complex; soaking for too long or too short periods of time worsens the diffraction quality of the complex.

According to a second aspect of the present invention, there is provided a method for assessing in-situ crystal formation in a test sample, the method comprising the steps of: obtaining optical image data from the test sample with optical imaging means; computing an optical image quality parameter from the optical image data; moving the test sample from the optical imaging means to X-ray diffraction apparatus in dependence on the optical image quality parameter; obtaining X-ray diffraction data from the test sample with the X-ray diffraction apparatus; computing an X-ray diffraction quality parameter from the X-ray diffraction data; and, computing a crystallographic aptness parameter from the optical image quality parameter and the X-ray diffraction quality parameter, the crystallographic aptness parameter being a measure of the suitability of crystalline material in the test sample for subsequent harvesting and X-ray crystallography.

BRIEF DESCRIPTION OF THE DRAWINGS

An example of the present invention will now be described in detail with reference to the accompanying drawings, in which:

FIG. 5 illustrates the steps taken in an automatic mode of operation in accordance with the present invention;

FIG. 6 illustrates the steps taken in an optical imaging analysis in accordance with the present invention;

DETAILED DESCRIPTION

Figure 1:
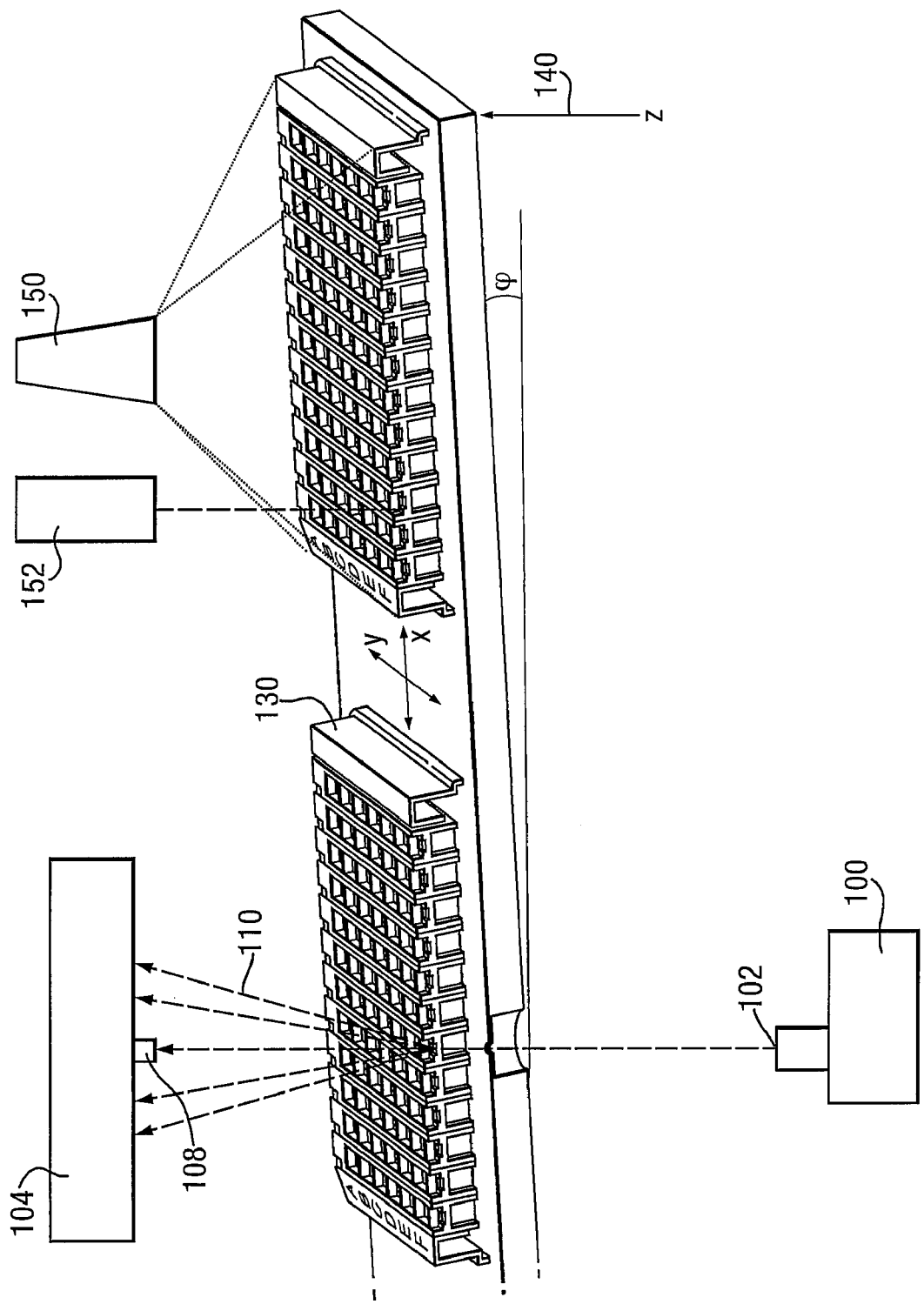
FIG. 1 shows a schematic illustration of the present invention.

As shown in the schematic of FIG. 1, the screening apparatus comprises an X-ray source 100 that generates a collimated beam of monochromatic X-rays 102. Typically the wavelength of the beam corresponds to the characteristic emission lines of copper Kα X-ray radiation or molybdenum Kα X-ray radiation. In its preferred embodiment, the X-ray source 100 comprises a sealed tube fine focus X-ray source or a sealed tube microfocus X-ray tube, but it may also comprise a rotating anode X-ray source or other source of X-rays. In its preferred embodiment, the X-ray source 100 comprises a shutter to control the exposure of the X-rays, and an optical assembly such as a multilayer optic, but it may also include other optical components such as polycapillary, monocapillary, and graphite optics. The X-ray beam 102 is approximately 200-300 microns in diameter and may be arranged to impinge in the vertical or horizontal planes, however a smaller or larger X-ray beam diameter may also be used.

The system also comprises an X-ray detector 104 which is located opposite the X-ray source 100 such that a solid angle of X-rays radially symmetric with the direct beam may be recorded. In its preferred embodiment, the detector 104 is a phosphor screen coupled to a charge-coupled device (CCD) detector. However, any other X-ray area detectors may be used, including multi-wire proportional counters, image plates and the like. A beamstop 108 is located at short distance in front of the detector 104 in order to block the direct beam from damaging the detector. The X-ray source 100, beamstop 108, and detector 104 are all fixed with respect to one another.

A container 130, possibly containing crystals in-situ, may be inserted into the system. Note that any type of crystal-growing container may in principle be used, but typically this will be a 24-well or 96-well plate or derivative thereof. Multi-well containers may be of the sitting-drop, hanging-drop, microbatch, or other type of crystal growing container. In FIG. 1 the container 130 is represented by a section through a 96-well plate and the container 130 is shown in two possible positions within the system. The container 130 is clasped in a translation device which allows motor-controlled translation in the x and y directions, as shown in FIG. 1.

Preferably, this invention also provides for a motorised rotation of the entire x-y assembly via translation in the z direction of an actuator as indicated by the arrow 140, which results in a rotation of the container about the y-axis. The axis of rotation intersects with the point at which the X-ray beam 102 impinges on the container 130 and is perpendicular to the X-ray beam 102. This rotation provides the mechanism for scanning the container 130 about the angle ø shown in FIG. 1, and which is required in order to record oscillation images of objects in the X-ray beam 102.

The container 130 may be translated in the x and y plane in order to bring any part of the container to intersect with the X-ray beam 102 The container 130 may also be translated in the x and y plane in order to bring it into the field of view of an optical microscope 150. Though FIG. 1 shows the container 130 both in position for optical analysis and for X-ray diffraction, it is important to bear in mind that the container will, in actual fact, only be in one position at any given time. In its preferred embodiment, the microscope 150 is a video microscope with a CCD imager. The microscope 150 is able to image the entire multi-well container to provide the user with an overall image of the container within the enclosed system.

An individual well of the container may be imaged under high magnification by a second microscope 152. The second microscope 152 enables the individual droplets containing the crystalline material to be imaged. Beneficially, the z translation caused by the actuator 140 (as shown in FIG. 1) is used to focus the images recorded by both the microscopes 150 and 152.

Finally, the entire system is enclosed in a radiation-proof enclosure and is air-conditioned to provide a controlled environment for the crystalline material in the container 130. As would be clear to one skilled in the art, other means of controlling the temperature of the air within the screening apparatus may also be used in accordance with the present invention.

In a manual mode of operation a single container 130 may be viewed by the optical microscopes 150 and 152 to identify one or many co-ordinates within the container 130 which may be queued for exposure to the X-ray beam 102. In the preferred embodiment, the image from the optical microscope is displayed on a computer, and a movable circular graphic is superimposed on the image to indicate the position and the diameter of the X-ray beam that the co-ordinate will be exposed to. In an automatic mode of operation, the image from the optical microscope 152 is analysed and one or many co-ordinates are automatically queued for exposure to the X-ray beam. In both modes of operation, selected co-ordinates within the container 130 are then mapped onto x and y translations such that the container 130 is re-positioned to bring the co-ordinates to intersect with the X-ray beam 102. An X-ray exposure is then made, controlled by the shutter within the X-ray source 100 at the same time that the container is rotated through an angle ø which is effected by the actuator 6 moving in the z direction. Characteristic scattering of the X-rays 110 will be generated from materials intersecting with the X-ray beam 102 which may be recorded on the detector 104. If crystalline material is present, this will generate a diffraction pattern of spots generated by Bragg diffraction from the crystal planes and this diffraction pattern may be analysed. The angle that the scan subtends in ø will determine how many X-rays meet the Bragg condition for diffraction from the crystalline material intersecting the X-ray beam 102. The ability to perform X-ray oscillation scans in ø of the container 130 is of great utility in the subsequent analysis of the recorded diffraction patterns, allowing more accurate quantitative assessments of the diffraction quality of a given crystal sitting in the container 130.

Figure 2:
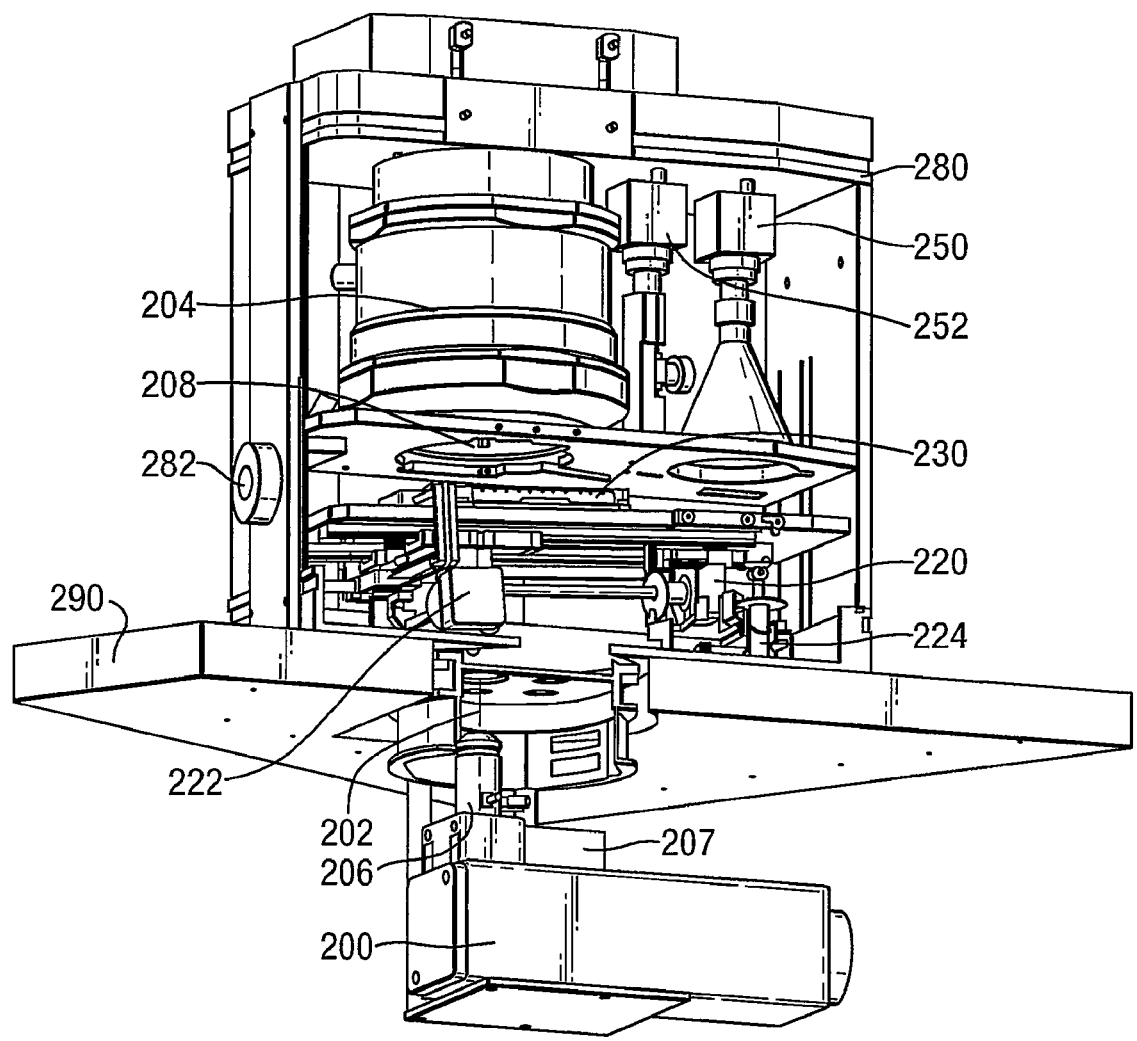
FIG. 2 shows a perspective view of a preferred embodiment of the preferred invention.
Figure 3:
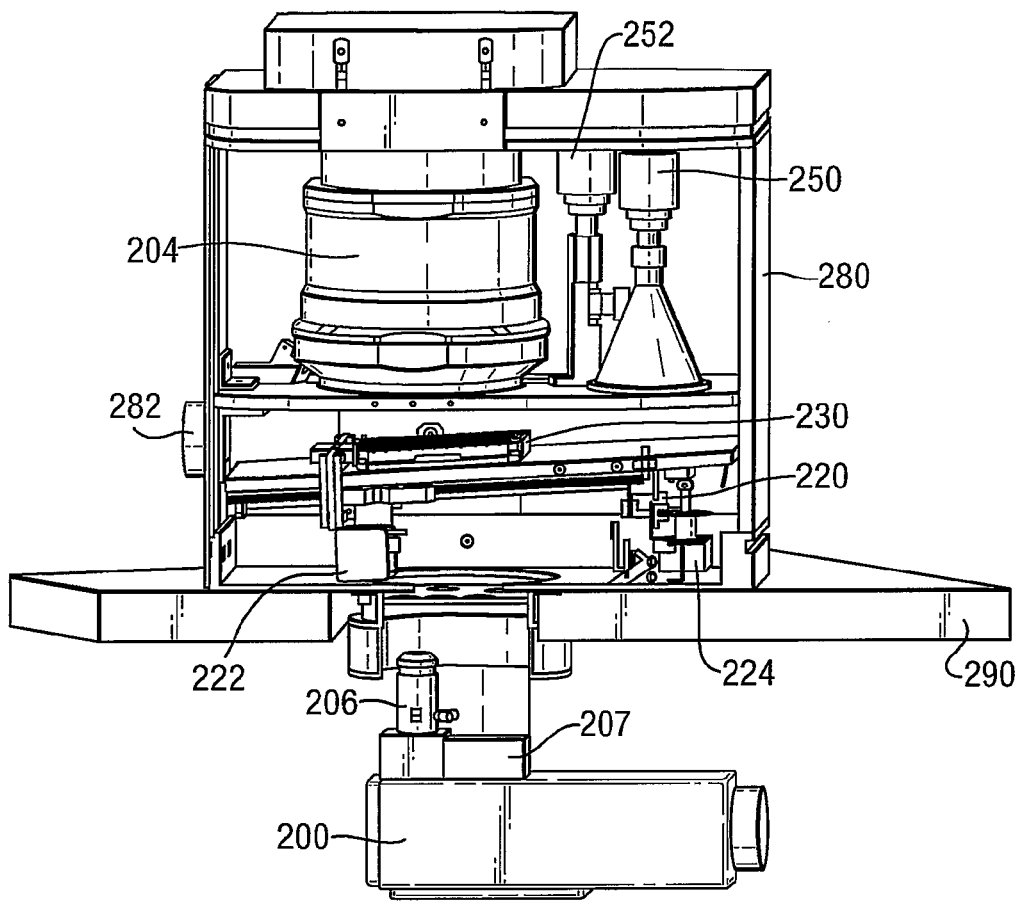
FIG. 3 shows a side on view of the preferred embodiment of the present invention.

FIGS. 2 and 3 show a physical embodiment of the present invention. FIG. 2 shows a perspective view while FIG. 3 shows the apparatus from side on. The arrangement of the X-ray source 200, X-ray beam 202, CCD detector 204, and beam stop 208 is illustrated on the left hand side of the Figures, while the first and second optical microscopes 250 and 252 are shown on the right hand side. The container 230 in this embodiment is a 96-well plate and is illustrated in position for X-ray analysis. A radiation proof container 280 surrounds the active components and the apparatus is mounted onto a work surface or table top 290. A port 282 allowing conditioning of the sample environment may be included in the design of the radiation proof container 280.

As would be clear to one skilled in the art, various X-ray optics 206 will be employed by the present invention, along with a shutter 207.

The locations of the motors 220, 222 and 224 for adjusting the location of the container 230 are also shown in FIGS. 2 and 3. Motors 220 and 222 are used to translate the container in the x and y directions respectively, while motor 224 is a tilt motor used to adjust the angle ø. In this context x, y, and ø are defined in the same way as they were in FIG. 1.

Figure 4:
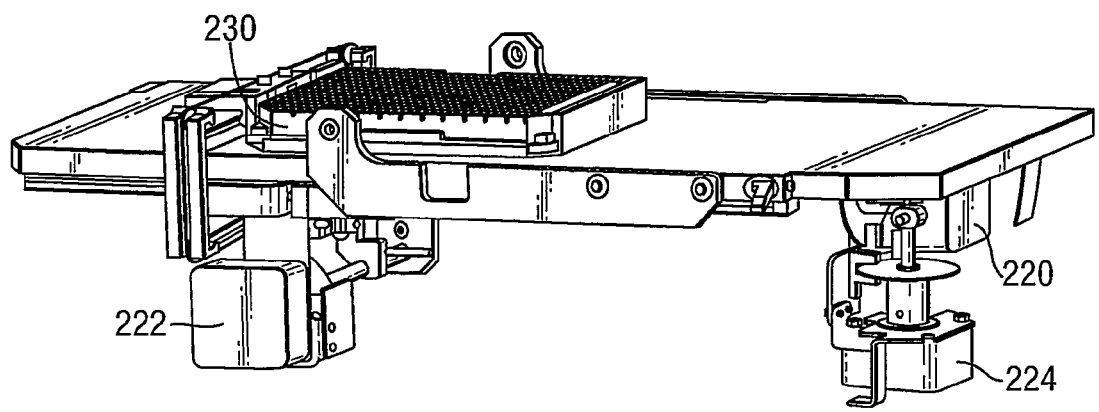
FIG. 4 shows a perspective view of the translation stage of the preferred embodiment of the present invention.

FIG. 4 shows an expanded view of the arrangement, in this embodiment, of the motors 220, 222, and 224 along with the translation stage upon which the container 230 lies.

The apparatus and software has three main modes of operation: automatic, interrupt and review, and we will now consider these in turn.

In automatic mode, the apparatus is driven from a system operation queue, where an individual operation may be one of: move motors to a certain position; move motors to a certain position and then record, store and analyse a video image; move motors to a certain position, then record a set of X-ray diffraction oscillation images while moving motors, and then store and analyse the images.

Operations are added to the queue with one of four priorities: immediate-priority operations will be added to the front of the queue, and the current operation interrupted (for example, ejecting the plate will cancel any operation in progress and drive the plate to the exit position); high-priority operations are added to the queue after existing high-priority operations; medium-priority operations are added to the queue after high-priority operations, and after existing medium-priority operations; low-priority operations are added to the queue after high- and medium-priority operations and after existing low-priority applications.

In the preferred embodiment, the automatic mode of the system is used as illustrated by FIG. 5:

501 and 502: A plate is inserted and identified to the system by means of a barcode scanner, or manually entering a unique plate identifier.

503: The date and time of the last video image of each well is retrieved from the database, and if older than a user-defined period, $t_1$, a new image is scheduled to be recorded by adding it to the queue with high-priority. Otherwise, if the date of the last video image is older than a shorter user-defined period, $t_2$, a new image is scheduled to be recorded by adding it to the queue with low-priority. The images are further prioritised within the queue so that the wells with no images or the oldest images will be the first to be recorded. In the preferred embodiment, $t_1$ is user-defined and defaults to 24 hours, and $t_2$ is user-defined and defaults to 1 hour.

504: The date of the last set of X-ray diffraction images of in-situ objects is retrieved from the database and if older than a user defined period, $t_3$ a new set of X-ray diffraction images is scheduled to be recorded by adding an operation to the queue with medium-priority. In the preferred embodiment, $t_3$ is user-defined and defaults to 24 hours.

505: The queue processing commences as soon as the queue contains an operation to be carried out.

In the automatic mode, all wells are automatically scheduled for video imaging unless individual wells, rows or columns are manually excluded from the experiment (for example, if the crystallisation experiment is only set up in two rows of an eight row plate, then all other rows may be excluded to save video imaging time). As can be seen in FIG. 6, after a video image of a well has been recorded (step 601) in-situ objects are detected in the video images by means of digital image processing algorithms and are classified and scored according to how likely they are to diffract (step 602), and their Crystallographic Aptness, and this data is subsequently stored in a database (step 603). In-situ objects are subsequently stored in the database and associated with a position in a given well and plate.

Figure 7:
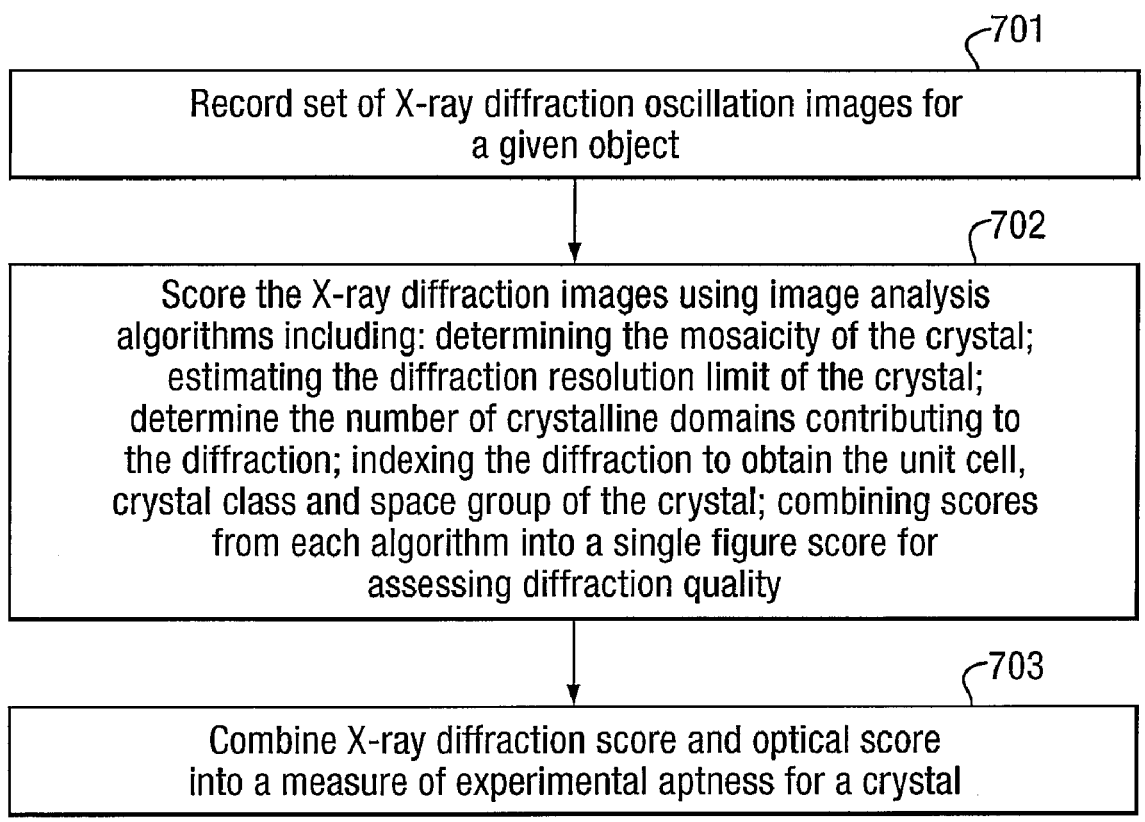
FIG. 7 illustrates the steps taken in an X-ray diffraction analysis in accordance with the present invention.

Finally, in automatic mode, in-situ objects associated with a given plate are retrieved and queued for X-ray diffraction measurement with a priority dependent upon both the score from optical classification and, if it exists, the score from analysis of a previous set of X-ray diffraction images. This prioritization increases the probability of collecting the most useful data first. As can be seen in FIG. 7, after a set of oscillation images has been collected for a sample (step 701) the images are scored on a number of criteria (step 702) to create a score representing diffraction quality. The scores for optical image quality and X-ray diffraction quality are then combined to create an overall Crystallographic Aptness score (step 703).

In interrupt mode it is possible to circumvent the prioritization. However, adding operations to the queue does not interrupt the current operation unless they are added with immediate-priority. In interrupt mode, the user is manually examining images and results from the plate that is currently inserted; the automatic generation and processing of an operation queue, which is running in the background, is temporarily interrupted in order to perform an immediate operation for the user.

If the user selects a well in the current plate, and no recent image for that well is available in the database, then the current background operation is interrupted by adding an immediate-priority operation to the head of the system queue. As a result, the plate is moved to the position for recording an image of the selected well and to record and store the image.

If the user chooses to eject a plate, the current operation is cancelled and the plate is moved to the exit position of the apparatus. In this case, the rest of the queue is erased, as it will be regenerated automatically when the plate is next inserted.

Finally, a review mode is provided whereby the software allows users to review data from all plates that have been examined in the apparatus. In review mode, the user may choose to modify the properties of in-situ objects associated with the plate.

For example:
1. the priority for measuring a set of X-ray diffraction images of the in-situ object may be changed, or the in-situ object may be flagged so that it will not be included in the X-ray diffraction operation queue that is generated.
2. the parameters of the set of X-ray diffraction images may be altered: the number of images in the set; the angle through which the apparatus rotates the crystal during X-ray exposure; and the length of the X-ray exposure In review mode, the user may choose to define new in-situ objects in a well for subsequent automatic measurement and analysis of a set X-ray diffraction images. The user may also choose to remove the definition of existing in-situ objects in a well, overriding the automatic identification of such an object.

An important aspect of the system is determining a "Crystallographic Aptness" for each sample under test. The Crystallographic Aptness score provides a measure of the suitability of crystals for experimental molecular structural analysis by X-ray crystallography. In the preferred embodiment the Crystallographic Aptness score is obtained by combining an Optical Image Quality score and an X-ray Diffraction Quality score in an additive manner according to equation (1).

$$\text{Crystallographic Aptness} = \alpha_1 \times \text{Optical Image Quality} + \alpha_2 \times \text{X-ray Diffraction Quality} \quad (1)$$

The coefficients $\alpha_1$ and $\alpha_2$ may be selected to give different weight to the Optical Image Quality of X-ray Diffraction Quality depending upon the application. Of course, it is possible to combine the scores in many other logical or functional ways to obtain a Crystallographic Aptness score, including a nonlinear functional relationship.

In order to calculate the Crystallographic Aptness it is necessary to define an Optical Image Quality parameter for scoring crystalline objects. In the preferred embodiment, the overall score of optical image quality of putative crystalline material in optical images is a combination of many separate measures obtained optically, as indicated by equation (2).

$$\text{Optical Image Quality} = \beta_1 \times \text{sharpness} + \beta_2 \times \text{straightness} + \beta_3 \times \text{shape} + \beta_4 \times \text{size} + \beta_5 \times \text{purity} + \beta_6 \times \text{separation} \quad (2)$$

where sharpness is a measure of the sharpness of object edges; straightness is a measure of how straight the objects edges are; shape is a measure of the crystal shape; size a measure of the crystal size; purity is a measure favouring crystals with fewer re-entrant angles and containing fewer separate regions; and, separation is a measure of the proximity to other objects in the drop. The coefficients $\beta_1$ to $\beta_6$ may be selected to give different weight to the optical image quality depending upon the application. In another embodiment the measures may also be combined in a different function to obtain a measure of Optical Image Quality.

Analysis of images obtained from optical microscopy may be broken into two distinct stages: pre-processing; analysis and scoring.

The pre-processing stage involves: detection of the shape of a drop, so that subsequent analysis is carried out on only the relevant portion of the image; and detection of the boundaries of putative crystals within the drop.

The drop, and putative crystals within the drop, may be identified by a method of image segmentation, wherein each pixel in an image is assigned to one or more separate regions, which ideally correspond to real objects within the image.

For analysis and scoring, only regions within the drop are considered. An area slightly larger than the region of each object is analysed in order to generate the first two measures of optical image score described above.

A sharp edge results in a sharp peak in the intensity in the first derivative of the image. The set of pixels of the first derivative of the optical image, p', in the vicinity of the detected edge of the object are considered together. The sharper the edge, the more concentrated the intensity is in a small number of pixels. Therefore, one measure of sharpness may be defined according to equation (3). The measure is independent of the length of the crystal boundary and the relative intensity of pixel values in the original image.

$$\text{sharpness} = \frac{1}{p_{total}'^2} \sum_i p_i'^2 \qquad (3)$$

The straightness of the edges of the crystal is encapsulated by a measure of the first derivative of the tangent at each point along the edge, known as the curvature. The straightness can be assigned a score by calculating the proportion of the boundary along which there is no significant change of direction, i.e. points where the first curvature is below a given threshold. A smoothing operator is applied to the curvature calculation to remove high frequency artifacts of pixel sampling, which otherwise have a detrimental effect on the calculation of the first derivative.

$$\text{straightness} = \frac{1}{L} \sum_{i=1}^{L} m_i \begin{bmatrix} m_i = 1 & \text{if } c_i < c_{threshold} \\ m_i = 0 & \text{if } c_i \geq c_{threshold} \end{bmatrix} \qquad (4)$$

where $c_i$ represents the curvature measured at each point i along the length of the crystal perimeter, L.

The shape of a crystal is also important. A measure of the shape of a crystal, which encapsulates its suitability for crystallographic study, is given by equation (5).

$$\text{shape} = \frac{\text{area}}{(0.25 \times L)^2} \qquad (5)$$

where L is the length of the perimeter of the crystal. Under this definition, objects with very long perimeters relative to their area receive a low score.

A measure of the size of a crystal, which reflects its suitability for crystallographic study, may be derived from its volume. Equation (6) estimates the volume from a two-dimensional image, and reaches a maximum for crystals with a volume of more than v, where v is typically 125000 μm³.

$$\text{size} = \min\left(1, \frac{\text{area}^{3/2}}{v}\right) \qquad (6)$$

where area is specified in μm².

The presence of internal boundaries and re-entrant angles in a crystal, which could correspond to impurities, twinned or inter-grown crystals can be detected by analysing the number of detected regions that lie within the convex hull of the primary region of the object. A measure called purity is used, as defined by equation (7), which is unity if no additional regions are detected within the convex hull of the object being analysed and tends to zero as the number and size of internal regions increases.

$$\text{purity} = \max\left(0, 1 - \left[\frac{\sum_j m_j^2}{t \times n_{object}^2}\right]\right) \qquad (7)$$

where $n_{object}$ is the number of pixels in the primary region, $m_j$ is the number of pixels in the $j^{th}$ impurity region; and t is a scaling factor. If t=1, and a single impurity region is equal to or larger in area to the primary region, then the purity score will be zero.

The proximity of an object to others in the drop decreases its suitability for crystallographic analysis, as it will be more difficult to harvest from the drop. A measure of separation, as defined by equation (8), encapsulates this property.

$$\text{separation} = \min\left(1, \frac{d_{closest}}{d_{safe}}\right) \text{ or 1 if no other objects are detected.} \qquad (8)$$

where $d_{closest}$ is the shortest non-zero distance between the edge of the object and other objects detected in the drop, and $d_{safe}$ is the minimum clearance around an object which will allow the object to be harvested without interference from surrounding objects, typically a value of 250 μm is used.

Figure 8:
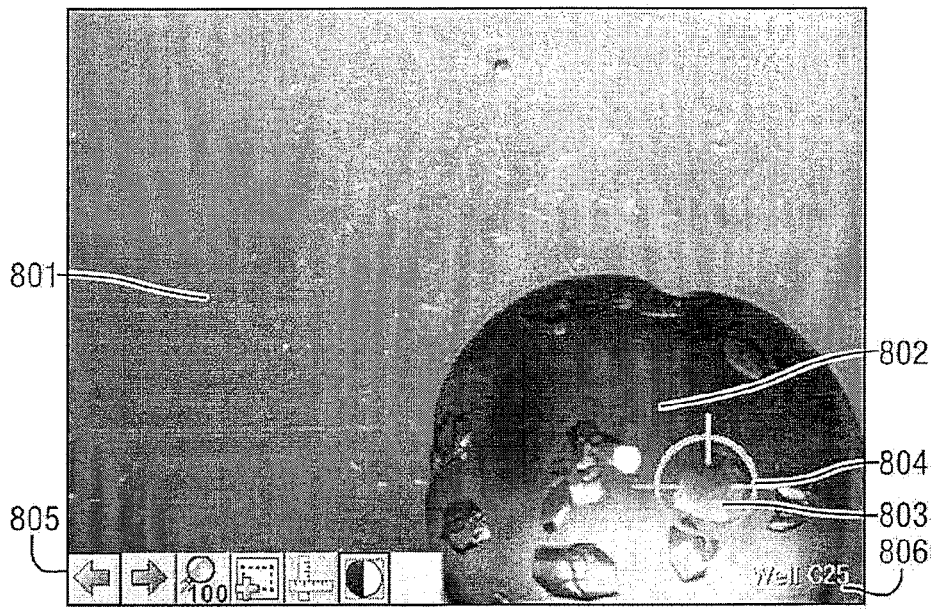
FIG. 8 shows a typical optical image that may be obtained in accordance with the present invention.

FIG. 8 shows a typical video microscope image recorded by the apparatus, as displayed in the control software. A drop of liquid 802 rests on the bottom surface of a well in the sample plate 801. Crystals have formed within the drop, as shown at 803, for example. A point can be selected for X-ray by clicking in the image. The point is represented by a 'cross-hair' graphic 804. When exposing this point to X-rays, the centre of the X-ray beam will correspond to the centre of the cross-hair graphic. The diameter of the circular part of the cross-hair corresponds to a diameter of 200 μm in the drop, which is the diameter of the X-ray beam in use in this embodiment of the apparatus. Additionally, the software overlays the image with a series of control buttons 805 for performing additional tasks, and some text 806 indicating the position of the well within the sample plate.

In order to calculate the Crystallographic Aptness it is also necessary to define an X-ray diffraction quality for scoring of X-ray diffraction images from the crystalline objects. In the preferred embodiment, the overall score of optical image quality of putative crystalline material in optical images is a combination of three separate measures, as defined by equation (9).

X-ray Diffraction Quality=$\gamma_1$×resolution+$\gamma_2$×mosaicity+$\gamma_3$×indexing (9)

where resolution is a measure of the highest angle at which diffraction can be detected; mosaicity is a measure of how well aligned the small crystalline domains are which constitute a single crystal; and, indexing is a measure of whether it is possible to find lattice parameters. The coefficients $\gamma_1$ to $\gamma_3$ may be selected to give different weight to the X-ray diffraction quality depending upon the application. In another embodiment the measures may also be combined in a different function to obtain a measure of X-ray diffraction quality.

The resolution measure in equation (9) corresponds to the highest resolution at which diffraction from a single crystal can be reliably collected. The reliability is assessed with a signal to noise threshold.

Crystals which have a high spread, or mosaicity, in the orientation of crystalline domains within a single crystal give rise to wider, less intense diffraction peaks. The greater the mosaicity, the less suitable a crystal is for X-ray diffraction analysis. Mosaicity is proportional to the full width at half the maximum of a diffraction peak, and can be estimated from a single X-ray diffraction image, or more accurately from several consecutive X-ray diffraction oscillation images.

Diffraction peaks from a single crystal are amenable to automatic indexing, whereby each peak is assigned a set of three integral indices corresponding to its position in reciprocal lattice of the crystal, provided that more than a small number can be detected. An indexing score is based on the fraction of peaks that can be indexed using a single crystal lattice. If the peaks cannot be indexed, a score of zero is obtained. If analysis of the peaks or the indexing suggests a salt crystal or a small molecule crystal, a score of zero is obtained.

Figure 9:
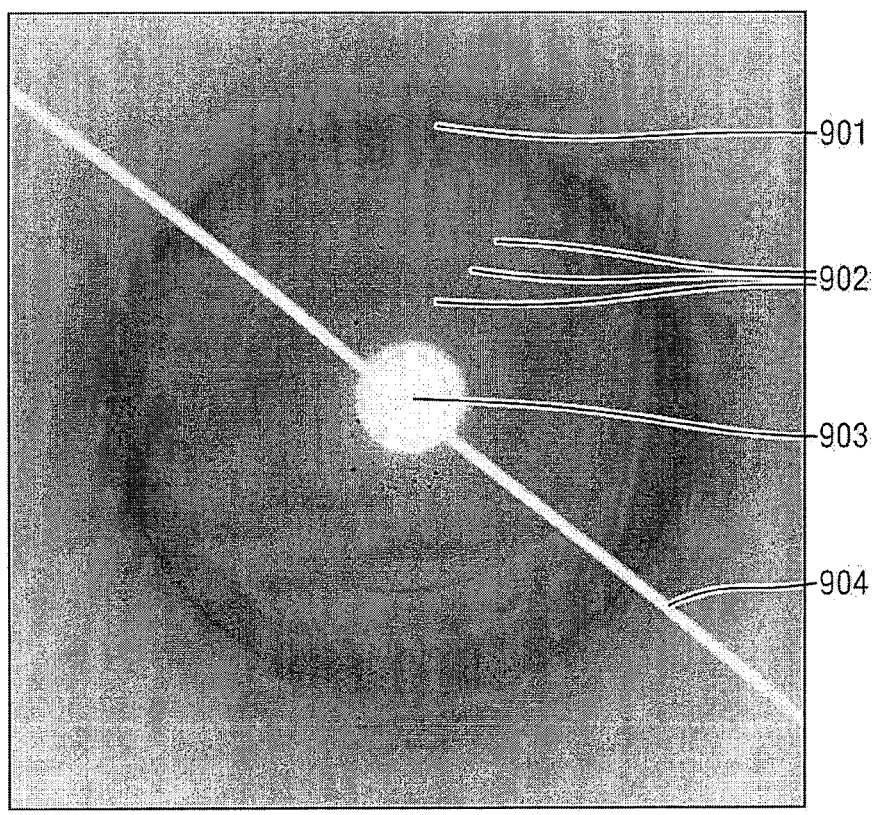
FIG. 9 shows a typical X-ray diffraction pattern that may be obtained in accordance with the present invention.

FIG. 9 shows a typical X-ray diffraction oscillation image obtained using the apparatus when the X-ray beam is incident on a crystal growing in solution in a well. The shade of each pixel in the Figure is proportional to the intensity of X-rays detected at the corresponding point on the detector, such that darker pixels represent a higher flux of X-rays. The crystal was rotated through an angle of 0.5 degrees while recording the image. X-rays are scattered from the sample plate and solution in which the crystal is growing resulting in dark circular bands, for example 901, consistent with the expected scattering from an amorphous sample. The crystal is exposed to X-rays and rotated through a small angle, bringing many planes into orientations, which satisfy the Bragg condition for diffraction and resulting in many sharp peaks in the image, for example at points 902. The image also contains areas of very low intensity X-ray scatter where the detector is shielded by the beamstop 903 and the beamstop support 904.

Figure 10:
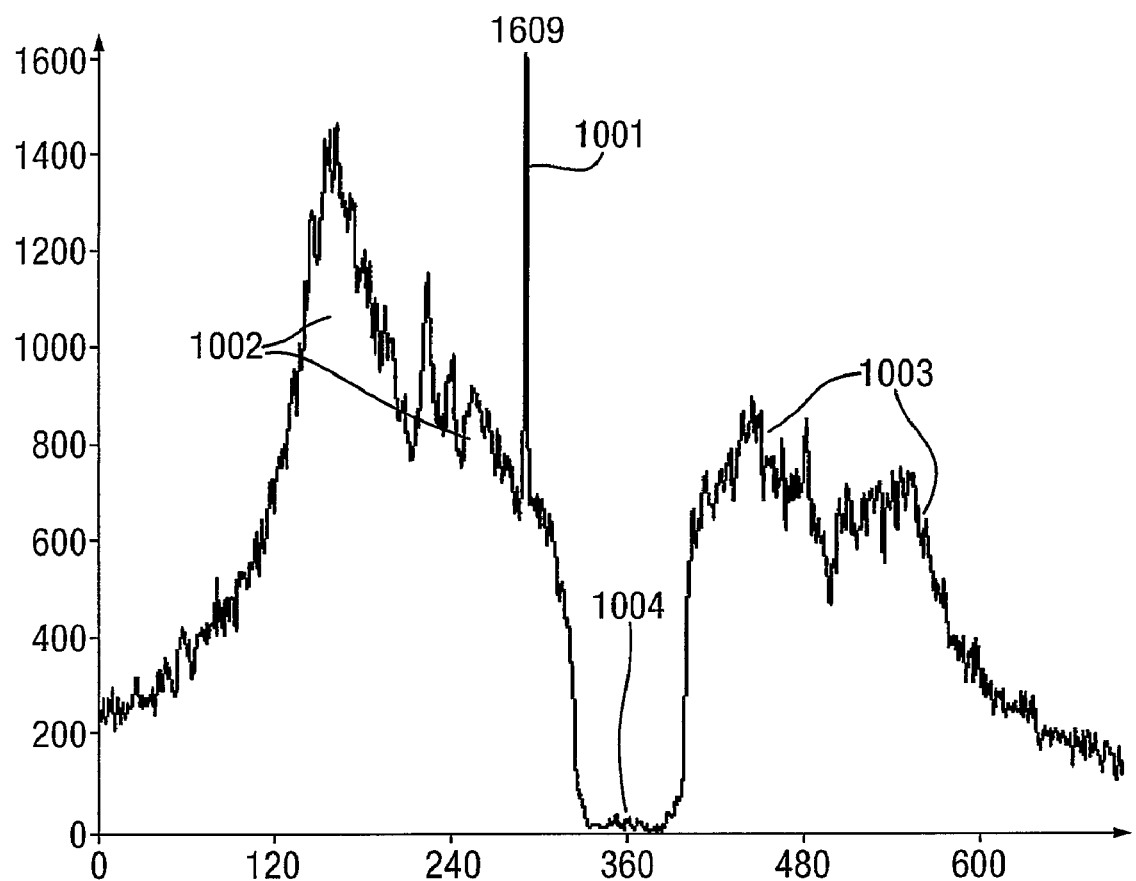
FIG. 10 shows a cross-section of a typical X-ray diffraction pattern that may be obtained in accordance with the present invention.

A cross-section of a typical X-ray diffraction image recorded using the apparatus is shown in FIG. 10. The relative detected X-ray intensity is plotted at each pixel along an arbitrary line, which passes through the centre of the image. The beamstop 1004 prevents significant X-ray intensity from reaching the detector directly behind it. The air, amorphous sample plate and liquid result in the broad X-ray scattering background 1002 and 1003. The relative number of X-rays detected at each pixel represents an integration of the total X-ray scattering from the sample, sample plate and liquid over the angle through which the plate is scanned. Diffraction from crystalline material gives rise to high intensity, sharp peaks 1001 as the diffracting planes of the material are rotated through an angle, which satisfies the Bragg condition.

Figure 11:
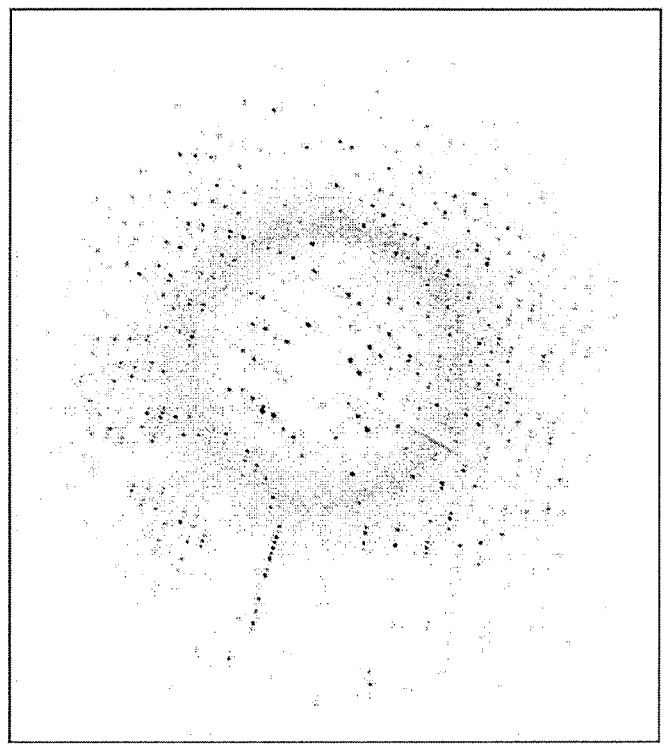
FIG. 11 shows a typical X-ray diffraction pattern adjusted to remove the effect of amorphous scattering that may be obtained in accordance with the present invention.

The result of an algorithm to remove the effect of amorphous scattering from the image in FIG. 9 is shown in FIG. 11. The processed image shows X-ray diffraction intensity from planes in a crystal without the amorphous background scattering from the air, sample plate and solution in which the crystal is growing. For each pixel in the original image, the algorithm computes the line perpendicular to the direction from the pixel to the centre of the image. Pixels distributed near this line, at a certain distance from the original pixel are sampled to obtain an estimate of the amorphous scattering in the local area of the detector. This value is subtracted from the original pixel value yielding the image shown in FIG. 11.

Figure 12A:
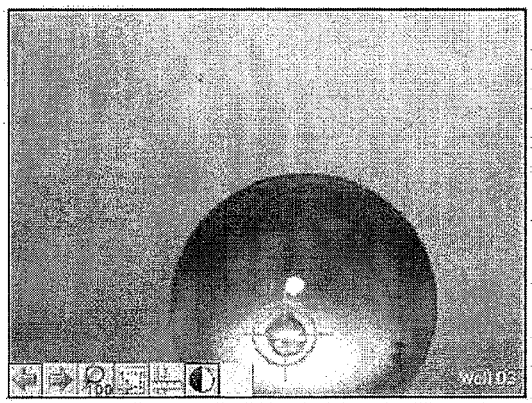
FIG. 12a shows an optical image obtained from a first example test sample in accordance with the present invention.
Figure 12B:
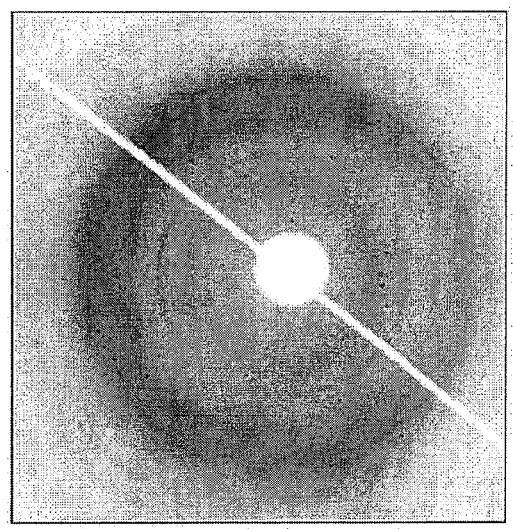
FIG. 12b shows an X-ray diffraction pattern obtained from a first example test sample in accordance with the present invention.

FIG. 12a shows a video microscope image and FIG. 12b an X-ray diffraction image from a good quality single crystal of lysozyme protein in a drop of solution. The crystal was exposed to the X-ray beam for 30 seconds while being rotated through an angle of 0.5°.

The Optical Image Quality is scored as follows: The boundary of the crystal is not very sharp and gives a sharpness measure of 0.42; the edges give a high straightness measure of 0.87; the shape measure is 0.76; the crystals is large enough to give a size measure of 1.0; the purity measure is 0.78 due to a separately classified small dark region near the lower end of the crystal; and, the separation measure is 1.0, as no objects are detected in the immediate vicinity. Thus, in the case where $\beta_1$-$\beta_6$ are equal and set to one sixth (0.1667), the Optical Image Quality measure from is 0.81.

The X-ray Diffraction Quality is scored as follows: The resolution limit is about 2.52 Å, giving a resolution score of 0.79; the mosaicity is small giving a mosaicity measure of 0.97; the indexing fits 94.1% of the diffraction peaks and gives the unit cell for lysozyme, resulting in an indexing score of 0.94. Thus, in the case where $\gamma_1$-$\gamma_3$ are equal and set to one third (0.3333), the X-ray Diffraction Quality measure calculated from equation (9) is 0.9.

Therefore, when the weighting parameters $\alpha_1$ and $\alpha_2$ in equation 1 are equal and set to one half (0.5), the Crystallographic Aptness of the crystals shown in FIG. 6 is 0.86. This is a high measurement of Crystallographic Aptness, and indicates that the crystal is suitable for further crystallographic study.

Figure 13A:
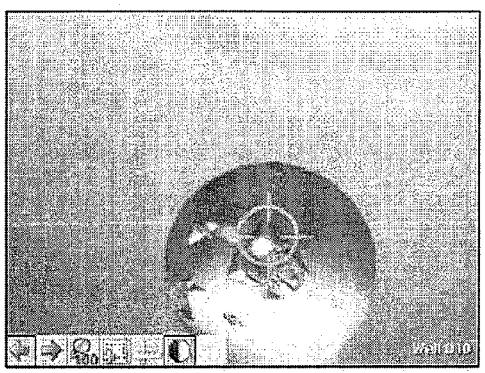
FIG. 13a shows an optical image obtained from a second example test sample in accordance with the present invention.
Figure 13B:
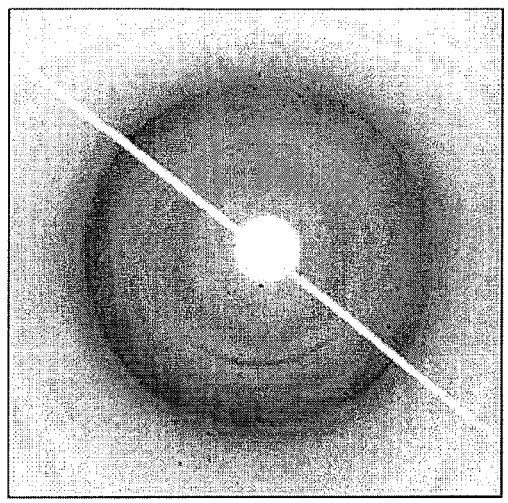
FIG. 13b shows an X-ray diffraction pattern obtained from a second example test sample in accordance with the present invention.

FIG. 13a shows a video microscope image and FIG. 13b an X-ray diffraction image from a cluster of lysozyme crystals in a drop of solution. The crystals were exposed to the X-ray beam for 60 seconds while being rotated through an angle of 0.5°. The diffraction pattern contains more spots than FIG. 6b due to the presence of more than one crystalline domain in the X-ray beam. Indexing successive subsets of the pattern determines the number of significant crystalline domains in the beam.

The Optical Image Quality of the crystal at the top of the cluster is scored as follows: The boundary of the crystal is quite sharp and gives a sharpness measure of 0.72; the edges give a high straightness measure of 0.91; the shape measure is 0.82; the crystal is large enough to give a size measure of 1.0; the purity measure is 0.32 due to penetration of regions from neighbouring crystals; the separation measure is 0.05 as several other objects are detected immediately neighbouring the crystal. Thus, in the case where $\beta_1$-$\beta_6$ are equal and set to 0.1667, the Optical Image Quality measure is 0.64.

The X-ray Diffraction Quality is scored as follows: The resolution limit is 2.1 Å, giving a resolution score of 0.95; the mosaicity is fairly low giving a mosaicity measure of 0.87; the indexing fits only 27% of the diffraction peaks with the unit cell for lysozyme, resulting in an indexing score of 0.27. Thus, in the case where $\gamma_1$-$\gamma_3$ are 0.3333, the X-ray Diffraction Quality measure calculated from equation (9) is 0.7.

Therefore the Crystallographic Aptness of the crystal shown in FIG. 7 is 0.66, when $\alpha_1$ and $\alpha_2$ are set to 0.5. This is medium measurement of Crystallographic Aptness primarily due to the proximity of other crystalline material in the drop. As such, it indicates that the crystal is likely to present problems, if harvested for further crystallographic analysis, but might suffice if no other suitable crystals can be grown.

Figure 14A:
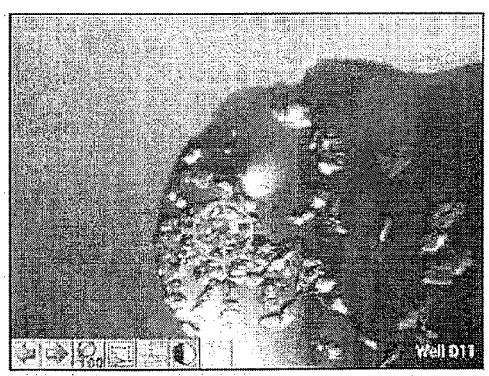
FIG. 14a shows an optical image obtained from a third example test sample in accordance with the present invention; and, FIG. 14b shows an X-ray diffraction pattern obtained from a third example test sample in accordance with the present invention.
Figure 14B:
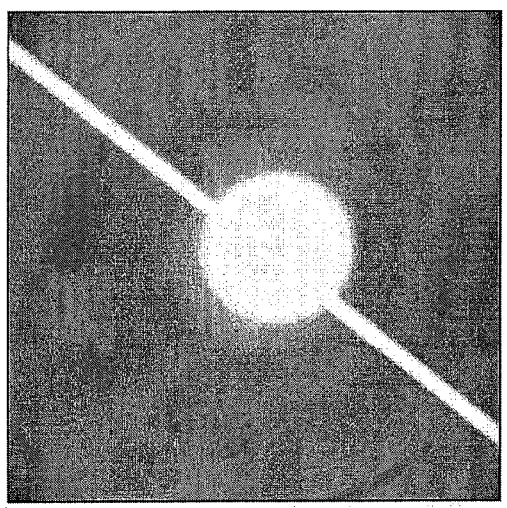

FIG. 14a shows a video microscope image and FIG. 14b an X-ray diffraction image from a cluster of tiny lysozyme crystals in a drop of solution. A crystal and its immediate neighbours were exposed to the X-ray beam for 600 seconds while being rotated through an angle of 0.5°. The diffraction pattern contains many more spots than either FIG. 12b or FIG. 13b due to the presence of many more crystalline domains in the X-ray beam. The spots are much weaker than the spots in either 11b or 12b because the volume of each crystalline domain is correspondingly smaller. It is usually not possible to automatically index subsets of the pattern in this type of case without a priori knowledge of the crystallographic unit cell of the material.

The Optical Image Quality of a crystalline region in the centre of the cluster is scored as follows: The boundary of the crystal is not very sharp and gives a sharpness measure of 0.52; the edges give a reasonable straightness measure of 0.74; the shape measure is 0.76; the crystalline region is small and gives a size measure is 0.13; the purity measure is 0.43 due to a few small sub-regions detected within the primary region; the separation measure is 0.02 as several other objects are detected very close to the crystal. Thus, in the case where $\beta_1$-$\beta_6$ are equal and set to 0.1667, the Optical Image Quality measure is 0.43.

The X-ray Diffraction Quality is scored as follows: The resolution limit is 11.0 Å, giving a resolution score of 0.18; the mosaicity is low giving a mosaicity measure of 0.53; the indexing fails to find any lattice consistent with the detected diffraction, due to the large number of crystalline orientations present giving an indexing score of 0.0. Thus, in the case where $\gamma_1$-$\gamma_3$ are 0.3333, the X-ray Diffraction Quality measure from Equation 9 is 0.24.

Therefore the Crystallographic Aptness is 0.34, where the parameters $\alpha_1$ and $\alpha_2$ are 0.5. This is a low measure of Crystallographic Aptness due to both the small size of the crystal, resulting in weak diffraction and the proximity of many other crystals in the drop. This score indicates that the crystal is unlikely to be suitable for harvesting and further crystallographic study.

The invention claimed is:

1. A screening apparatus for assessing in-situ crystal formation in a test sample, the apparatus comprising:
    optical imaging means for obtaining optical image data from the test sample;
    an X-ray diffraction apparatus configured to obtain X-ray diffraction data from the test sample, the X-ray diffraction apparatus and the optical imaging means mounted within a common housing; and
    processing means coupled to the optical imaging means and the X-ray diffraction apparatus, the processing means for computing an optical image quality parameter from the optical image data and an X-ray diffraction quality parameter from the X-ray diffraction data, the processing means for computing a crystallographic aptness parameter from the optical image quality parameter and the X-ray diffraction quality parameter, the crystallographic aptness parameter being a measure of the suitability of crystalline material in the test sample for subsequent harvesting and X-ray crystallography.

2. A screening apparatus according to claim 1, wherein the X-ray diffraction data comprises an X-ray oscillation image of the test sample.

3. A screening apparatus according to claim 1, further comprising:
    support means for mounting the test sample within the apparatus, the support means comprising integral translation means for moving the tests sample between the optical imaging means and the X-ray diffraction apparatus.

4. A screening apparatus according to claim 3, comprising a rotational axis defined by the intersection of the support means and the X-ray diffraction apparatus, wherein the translation means is adapted to move the support means parallel and perpendicular to the rotational axis.

5. A screening apparatus according to claim 4, wherein the X-ray diffraction apparatus comprises an X-ray source, and the rotational axis is perpendicular to a beam path from the X-ray source to the support means.

6. A screening apparatus according to claim 4, wherein the translation means is adapted to rotate the support means around the rotational axis.

7. A screening apparatus according to claim 1, wherein the optical image quality parameter depends on one or more of the following attributes of the test sample: sharpness, straightness, shape, size, purity, and separation.

8. A screening apparatus according to claim 1, wherein the X-ray diffraction quality parameter depends on one or more of the following attributes of the test sample: resolution, mosaicity, and indexing.

9. A screening apparatus according to claim 1, wherein the screening apparatus being further adapted to calculate the crystallographic aptness parameter of a plurality of samples within an array; and,
    wherein the processing means is adapted to control the order in which optical image data and X-ray diffraction data are obtained for samples within the array in dependence on one or more queue parameters.

10. A screening apparatus according to claim 9, wherein the queue parameters include one or more of the following: time elapsed since optical image data was last obtained for each sample, time elapsed since X-ray image data was last obtained for each sample, the optical image quality parameter of each sample, the X-ray diffraction quality parameter of each sample, the crystallographic aptness parameter of each sample.

11. A screening apparatus according to claim 1, further comprising temperature control means adapted to control the temperature of air within the screening apparatus.

* * * * *